United States Patent
Colvin, Jr. et al.

(10) Patent No.: US 8,223,325 B2
(45) Date of Patent: Jul. 17, 2012

(54) OPTICAL SENSOR ASSEMBLY

(75) Inventors: Arthur E Colvin, Jr., Mt. Airy, MD (US); Casey J. O'Connor, Gaithersburg, MD (US); Daniel C. Ferraro, Mt. Airy, MD (US)

(73) Assignee: Sensors for Medicine & Science, Inc., Germantown, MD (US)

( * ) Notice: Subject to any disclaimer, the term of this patent is extended or adjusted under 35 U.S.C. 154(b) by 342 days.

(21) Appl. No.: 12/563,396

(22) Filed: Sep. 21, 2009

(65) Prior Publication Data

US 2010/0073669 A1    Mar. 25, 2010

Related U.S. Application Data

(60) Provisional application No. 61/098,479, filed on Sep. 19, 2008.

(51) Int. Cl.
*G01J 3/00* (2006.01)
(52) U.S. Cl. ........................................................ 356/218
(58) Field of Classification Search ........................ None
See application file for complete search history.

(56) References Cited

U.S. PATENT DOCUMENTS

| | | | |
|---|---|---|---|
| 4,616,176 A * | 10/1986 | Mercure et al. | 324/127 |
| 5,517,313 A | 5/1996 | Colvin, Jr. | |
| 5,995,859 A | 11/1999 | Takahashi | |
| 6,014,577 A | 1/2000 | Henning et al. | |
| 6,015,386 A | 1/2000 | Kensey et al. | |
| 6,330,464 B1 | 12/2001 | Colvin, Jr. et al. | |
| 6,400,974 B1 | 6/2002 | Lesho | |
| 6,402,689 B1 | 6/2002 | Scarantino et al. | |
| 6,940,590 B2 | 9/2005 | Colvin, Jr. et al. | |
| 7,121,396 B2 * | 10/2006 | Rogner et al. | 192/85.51 |
| 7,135,342 B2 | 11/2006 | Colvin, Jr. et al. | |
| 2002/0026108 A1 | 2/2002 | Colvin, Jr. | |
| 2002/0197622 A1 | 12/2002 | McDevitt et al. | |
| 2006/0149143 A1 | 7/2006 | Colvin, Jr. | |
| 2008/0139904 A1 | 6/2008 | Colvin et al. | |

FOREIGN PATENT DOCUMENTS
EP    922433 A1    6/1999

* cited by examiner

*Primary Examiner* — Tu Nguyen
(74) *Attorney, Agent, or Firm* — Rothwell, Figg, Ernst & Manbeck, P.C.

(57) ABSTRACT

The present invention provides systems and methods for measuring an analyte in a medium without exposing the medium to contamination. The systems and methods employ a novel combination of a small sensor device embedded in a Luer cap and capable of wirelessly transmitting data to a reading device.

39 Claims, 10 Drawing Sheets

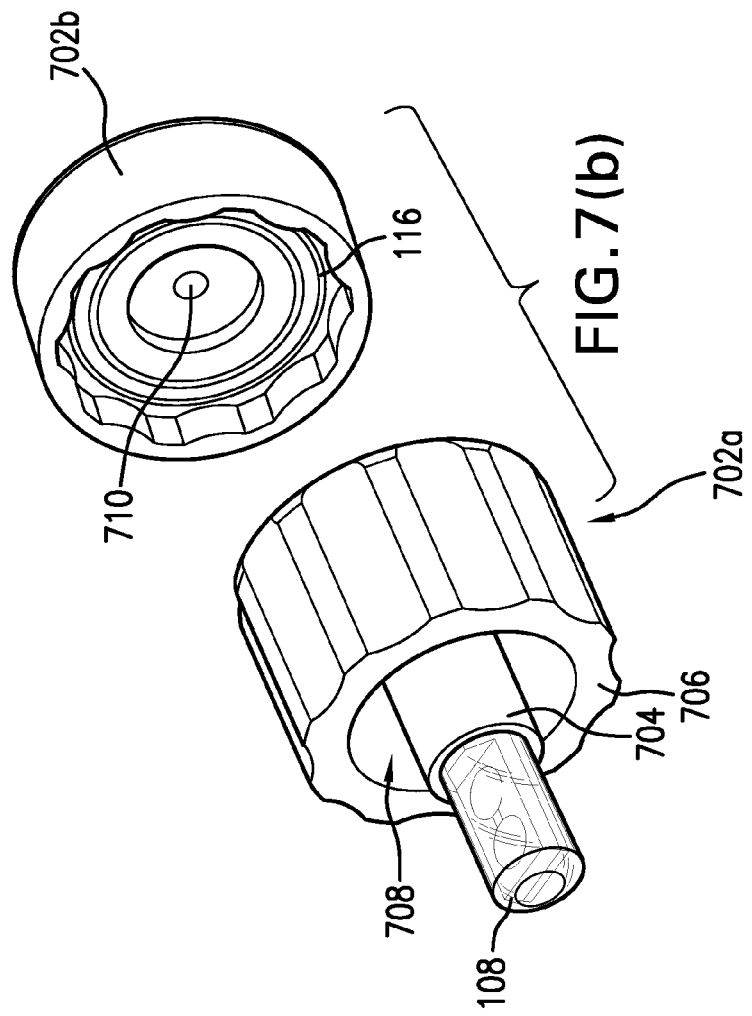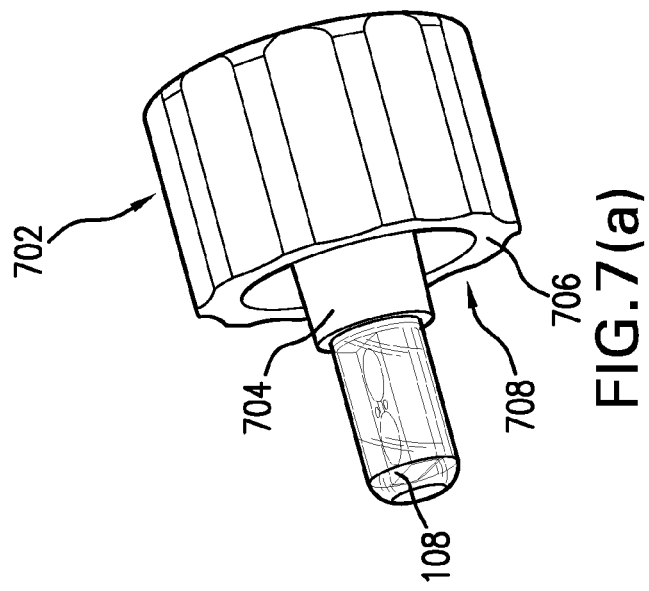

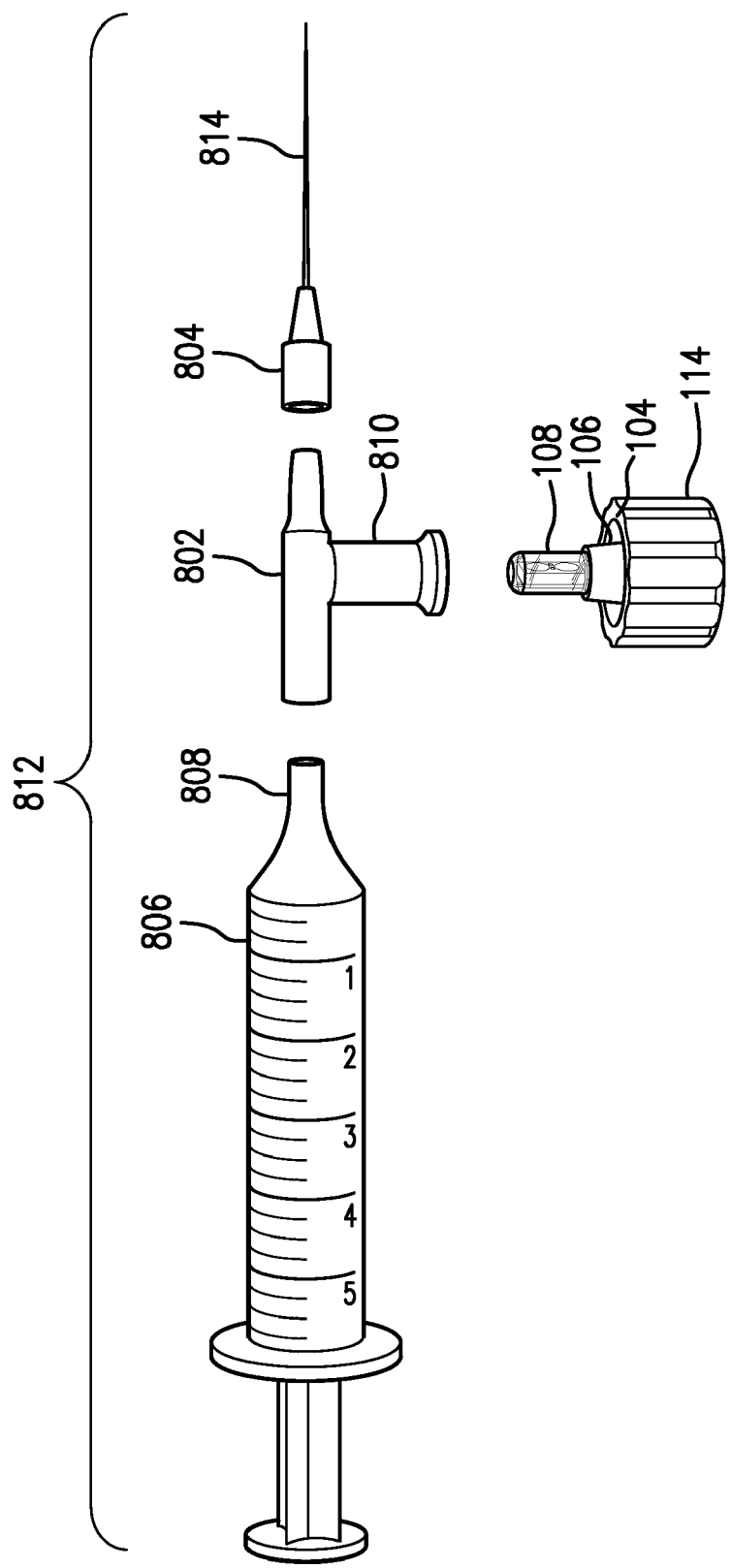

OPTICAL SENSOR ASSEMBLY

This application claims the benefit of U.S. Provisional Patent Application No. 61/098,479 filed on Sep. 19, 2008, the entire disclosure of which is incorporated herein by reference.

BACKGROUND

1. Field of the Invention

The present invention relates generally to devices, systems, and methods for measuring the presence of an analyte in a medium and, more specifically, to an optical sensing apparatus and housing permitting continuous exposure to the desired medium.

2. Description of the Related Art

Sensors for Medicine and Science, Inc. (SMSI) has developed a number of very small wireless sensors for monitoring various analytes (e.g., glucose, $CO_2$, $O_2$, etc.) present in a body or other medium. In certain embodiments, these very small sensors are adapted to be implanted into a human or animal to measure the presence, absence, or quantity of an analyte in the blood, wherein the sensor itself detects and measures an analyte within its immediate surroundings. The wireless sensors are described more fully in, for example, U.S. Pat. Nos. 5,517,313, 6,330,464, 6,400,974, 7,135,342, and 6,940,590, which are incorporated herein by reference in their entirety.

In certain embodiments, these very small implantable sensors are powered by induction from a primary coil contained within an external reader that is configured, for example, as a wristwatch, pager or other devices, and a secondary coil printed on the circuit substrate within the sensor itself. In certain embodiments, the sensor receives power, and transmits its data, via this primary and secondary coil electromagnetic link. See, for example, U.S. Pat. No. 6,400,974, which is incorporated herein by reference in its entirety.

Although one design application is human or animal implant monitoring, there is a need for new and improved wireless sensors and methods for using wireless sensors in a range of other applications to provide continuous measurement of an analyte in a medium.

SUMMARY

The present invention encompasses a sensing apparatus, systems and methods for permitting continuous exposure of an optical sensor to a desired medium for the purpose of measuring the presence of an analyte in the medium.

According to an embodiment of the present invention, a sensing apparatus is provided. The sensing apparatus includes a housing that has an external sleeve and a mating member housed within the external sleeve. An optical-based sensor capable of measuring the presence or intensity of an analyte in an analyte containing medium is disposed within the mating member of the housing. The sensor includes a body, internal circuitry, and an internal coil housed within its body. In some embodiments, the internal coil is configured to wirelessly receive electrical power from an external power supply. The sensing apparatus can also include drive circuitry configured to communicate power to and data from the sensor. According to some embodiments, the drive circuitry can be configured to communicate data to the sensor as well. The mating member is configured to mate with a device that is in contact with the medium containing the analyte to be measured such that the optical based sensor is capable of contacting the analyte containing medium.

According to another aspect of the present invention, a sensor system is provided. The sensor system includes a plurality of optical-based sensor for measuring the presence of an analyte in an analyte containing medium. Each of the sensors can be disposed in a housing having an external sleeve and a mating member housed within the external sleeve. The sensors can include a body, internal circuitry, and an internal coil housing within the body. The internal coil can be configured to receive electrical power from an external power supply and to transmit data.

The system, according to some embodiments of the present invention, may include at least one reading device. The reading device can be coupled to a primary coil, which is configured to transmit power to and receive data from the internal coil of the optical-based sensors. According to various embodiments of the present invention, the reading device may also be configured to transmit data to the optical-based sensors.

The system, according to some embodiments of the present invention, may also include a processing device configured to interface with the reading device in order to receive data from at least one of the sensors. Additionally, the processing device may send data to one of the sensors via the reading device according to various embodiments of the present invention. The mating member of the housing can be configured to mate with a device that is in contact with the medium containing the analyte to be measured such that the optical-based sensors are brought into contact with the analyte containing medium.

According to another aspect of the present invention, a method of measuring the presence and concentration of an analyte in a medium is provided. The method includes providing a sensing apparatus comprising a housing having an external sleeve and a mating member disposed within the external sleeve. The sensing apparatus can further comprise an optical-based sensor disposed within the mating member of the housing. The optical-based sensor can include a body, internal circuitry, and an internal coil housing within the body. The internal coil can be configured to receive electrical power from an external power supply. The method can further include mating the sensing apparatus with a device that is configured to be in fluid communication with the medium containing the analyte to be measured and exciting the internal coil by electromagnetic induction using a reading device. The method can also include the steps of receiving at the reading device data from the optical-based sensor relating to the presence of an analyte in a medium and transmitting the data to a processing device. The method may can also include the step of sending data to the sensor, according to some embodiments of the invention.

According to another aspect of the present invention, a sensing apparatus is provided which includes a housing having a cavity disposed in an outside surface of the housing. An optical-based sensor capable of measuring the presence of an analyte in an analyte containing medium can be disposed within the housing. The sensor can include a body, internal circuitry, and an internal coil housed within its body. The internal coil can be configured to receive electrical power from an external power supply. Drive circuitry can be configured to communicate power to and receive data from the sensor. The drive circuitry may also be configured to transmit data to the sensor according to some embodiments of the invention. The housing can be configured to connect with a device in contact with the medium containing the analyte to be measured such that the optical-based sensor is capable of contacting the analyte containing medium.

According to some embodiments of the invention, the sensor may further comprise a light source for introducing light into a fluorescent indicator that interacts with the medium. A photodetector can also be included within the sensor in order to detect light emitted by the fluorescent indicator in response to the introduced light. The photodetector can output a signal proportional to the detected light. The light emitted by the fluorescent indicator can vary in accordance with the presence and concentration of an analyte in the medium.

According to some embodiments of the invention, the drive circuitry may be further configured to communicate data from the sensor to an external processing device. This data can include the signal output from the photodetector according to some embodiments. Additionally, the drive circuitry may be configured to communicate data from the processing device to the sensor. According to various embodiments, the communication between the processing device and the drive circuitry may be wireless or the result of a physical connection (e.g., USB, serial cable, coaxial cable, transmission line, etc.) between the processing device and the drive circuitry.

According to some embodiments of the present invention, the primary coil can be printed on a PCB substrate and mounted within coupling distance of the internal coil. Additionally, according to some embodiments, the housing may be a luer fitting such as, for instance, a luer lock. The luer fitting can have a six percent taper according to some embodiments of the present invention, however, according to other embodiments the taper is different from six percent. The luer fitting can be configured to mate with devices in fluid or gaseous communication with a medium containing the analyte to be measured.

According to some embodiments of the present invention the analyte is glucose. According to various other embodiments, however, the analyte may be $CO_2$, $O_2$, NaCl, or biomarkers. According to various other embodiments, the sensor may also detect color, refraction index, pH, affinity recognize elements (such as antibodies), ion exchange, and covalent bonding. Additionally, the sensor can be configured to measure more than one analyte.

According to some embodiments of the present invention, the mating member is configured to mate with a syringe, or line carrying a fluid or gas. The mating member may also be configured to mate with containers, catheters, or tanks.

Further applications and advantages of various aspects and embodiments of the present invention are discussed below with reference to the drawing figures.

BRIEF DESCRIPTION OF THE DRAWINGS

FIGS. 7(a)-(c) illustrate a housing according to embodiments of the present invention.

FIG. 8 illustrates a sensor system according to embodiments of the present invention.

DETAILED DESCRIPTION OF THE PREFERRED EMBODIMENTS

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

Figure 1:
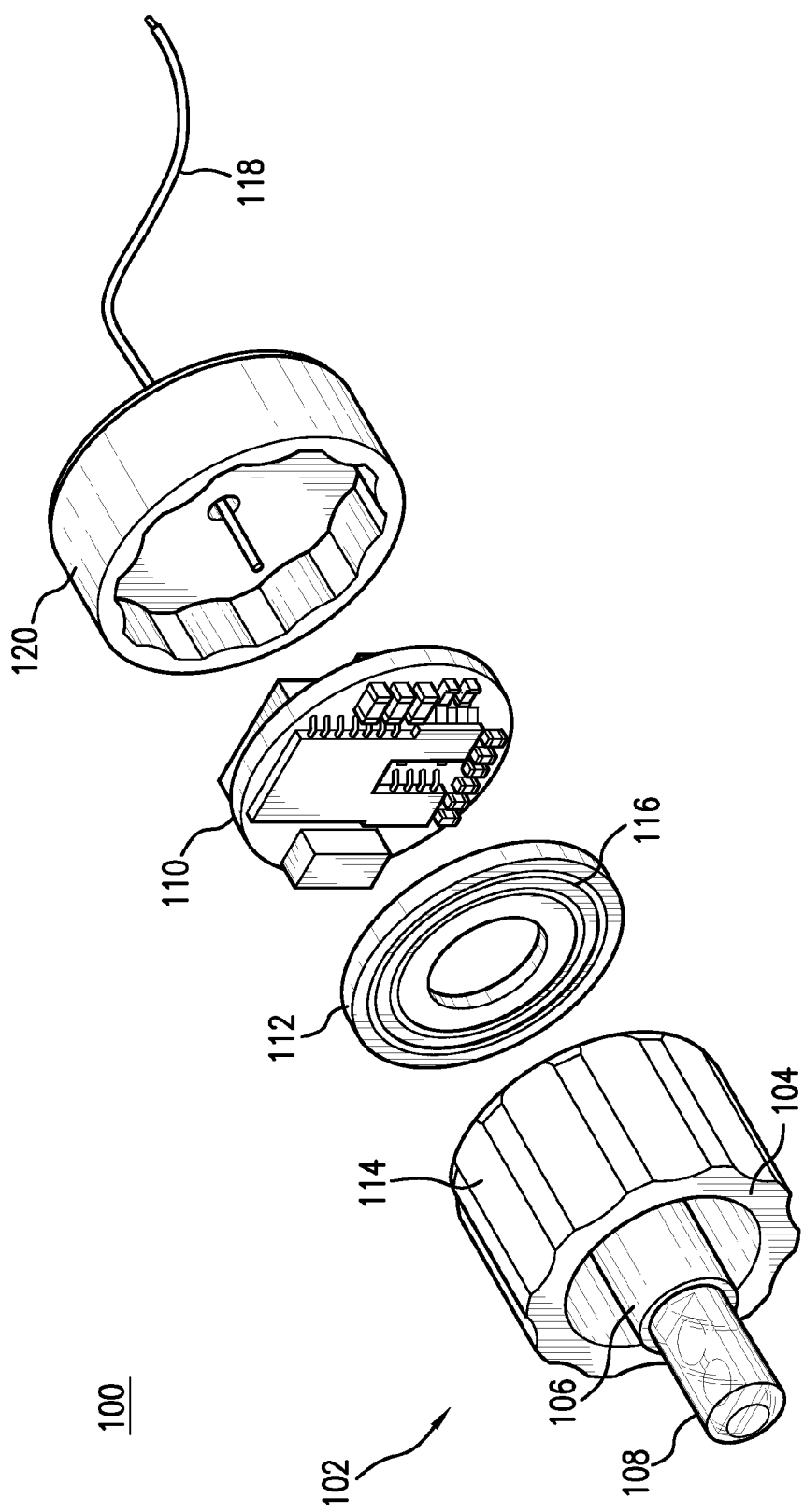
FIG. 1 illustrates a sensor assembly according an embodiment of the present invention.

FIG. 1 illustrates an exploded view of a sensing apparatus 100 according to embodiments of the present invention. The apparatus 100 can include a sensor assembly 102 that itself includes a housing 114 having an external sleeve 104 and a mating member 106 disposed within the external sleeve 104. In one embodiment, an optical sensor 108 can be disposed within the mating member 106 of the housing. A primary coil 116 can be mounted on a PCB substrate 112. Drive circuitry 110 can be coupled to the primary coil 112 in order to drive the circuit. Communications cable 118 can connect the drive circuitry to an external processing device. Housing cap 120 may be integrated with housing 114 or separate, as shown in FIG. 1. The primary coil 116 and drive circuitry 110 are preferably enclosed within the housing 114 and housing cap 120. According to some embodiments of the present invention, the sensor can be embedded into the inside of the housing a frictional fit. However, according to other embodiments, the sensor could be embedded within the housing an adhesive such as, for example, a silicone adhesive.

According to embodiments of the present invention, communications cable 118 can be replaced with an RF antenna or other means of wireless communication. According to other embodiments, the housing may be a standardized leak-free fitting such as, for example, a luer lock.

Figure 2:
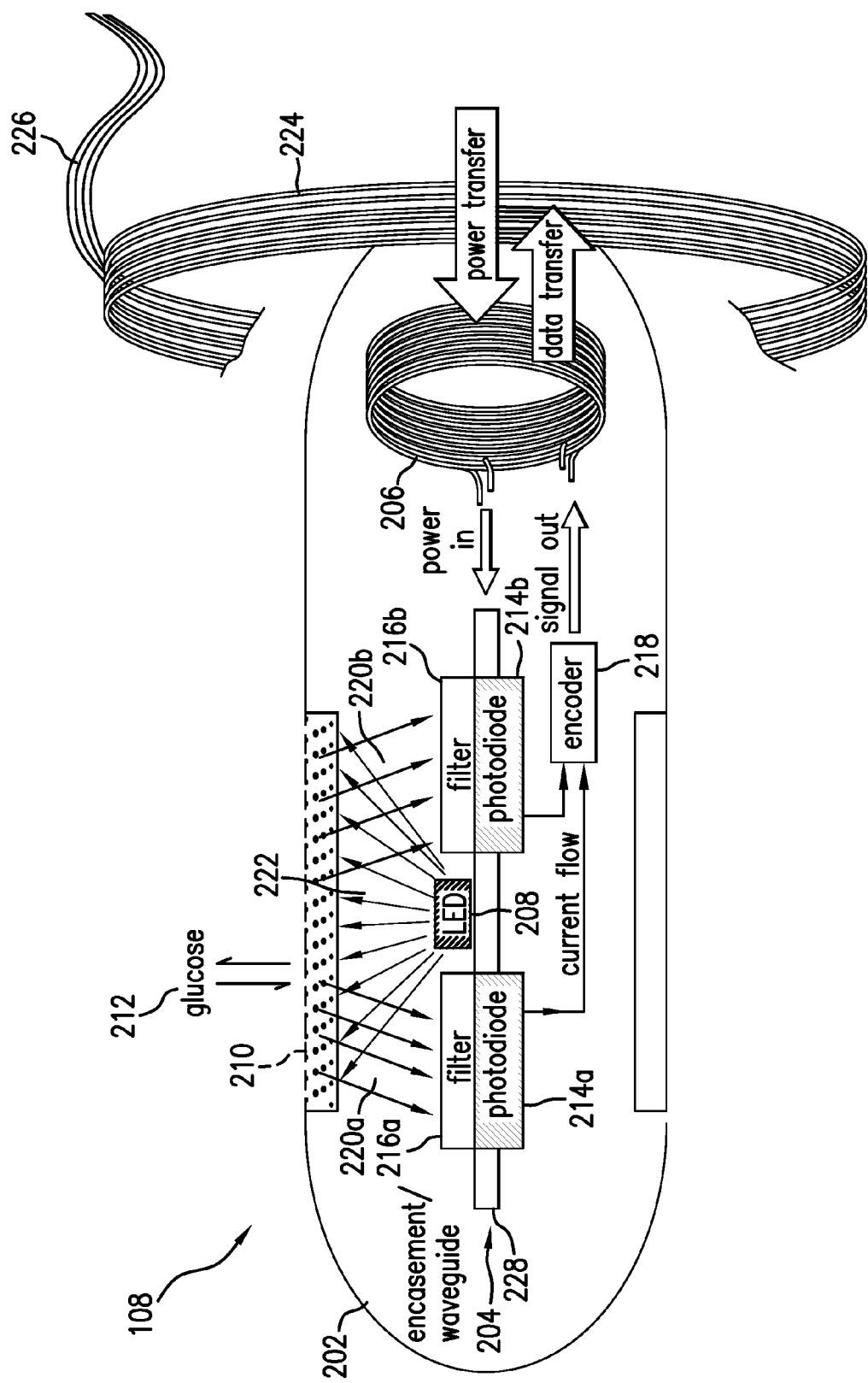
FIG. 2 illustrates a functional diagram of an optical-based sensor according to embodiments of the present invention.

FIG. 2 illustrates an optical-based sensor 108 according to embodiments of the present invention. In one embodiment, the sensor includes an encasement 202 forming a sensor body. According to some embodiments of the invention, the encasement 202 can function as an optical waveguide. Internal circuitry 204 is mounted on a substrate 228 and can include one or more photodiodes 214a and 214b, a light emitting diode (LED) 208, an encoder 218, and a wireless interface. According to some embodiments, photodetectors 214a and 214b are photodiodes. Filters 216a and 216b can be placed over photodiodes 214a and 214b.

In some embodiments, primary coil 224, which can be connected to the drive circuitry though connection 226, can be disposed within coupling distance of internal coil 206 in sensor 108. This enables the primary coil to transfer power to the internal coil 206 thorough electromagnetic induction. Once powered, the sensor can be configured to excite fluorescent indicator molecules 210 with excitation radiation 222 emitted by LED 208. Indicator molecules 210 react to the presence of an analyte 212 (e.g., glucose) in the medium surrounding the sensor 108 and, when excited by radiation 222, emit response radiation 220a and 220b (such as, for example, fluorescent radiation), which can be detected by the photodetectors 214a and 214b. The amount of response radiation 220a and 220b emitted varies as a function of the concentration of the analyte present in the medium. Filters 216a and 216b can be configured to block substantially all light in the spectrum of the excitation radiation 222 while allowing substantially all of the light in the spectrum of the response radiation 220a and 220b to pass.

The photodetectors 214a and 214b can produce an analog signal which, according to some embodiments, can be encoded as an amplitude modulated (AM) or frequency modulated (FM) signal by encoder 218. According to some embodiments of the invention, the encoder may also digitally encode the analog output from the photodetectors. The signal output by the encoder 218 can then be transferred to the internal coil 206, which, in turn, transfers the signal to the primary coil 224 through electromagnetic induction. According to some embodiments of the present invention, the primary coil 224 can be incorporated into a wristwatch. At any rate, the primary coil is oriented coaxially to the internal coil 224 in order to establish electromagnetic coupling according to embodiments of the present invention. According to other embodiments of the present invention, primary coil 224 can be placed immediately adjacent to the backside of housing 114, but within coupling distance of internal coil 206. In certain embodiments, the sensor receives power, and transmits its data, via the primary and secondary coil electromagnetic link as described in U.S. Pat. No. 6,400,974, which is incorporated herein by reference in its entirety.

Additional examples of the structure and operation of sensors 108 is are described in U.S. Pat. Nos. 5,517,313, 6,330,464, 6,400,974, 7,135,342, and 6,940,590, which are incorporated herein by reference in their entirety. For instance, U.S. Pat. Nos. 5,517,313, 6,330,464, 6,400,974, 7,135,342, and 6,940,590 describe the operation of a sensor capable of detecting the presence of an analyte using indicator molecules. Similarly, U.S. Pat. Nos. 6,330,464 and 6,400,974 describe the operation of the wireless powering and communications facility of a sensor.

While the sensor 108 illustrated in FIG. 2 depicts two photodetectors, any number of photodetectors could be used to allow the sensor to detect a number of different analytes. By increasing the number of photodetectors and altering the chemistry of the indicator molecules (for instance, by including multiple indicator molecules each of which responds to a different analyte), multiple analytes could be detected by a single sensor. According to some embodiments, each photodetector could have a different filter to accommodate a different wavelength of light emitted by different fluorescent indicator molecule 210, each of which can be configured to fluoresce at a different wavelength.

Figure 3:
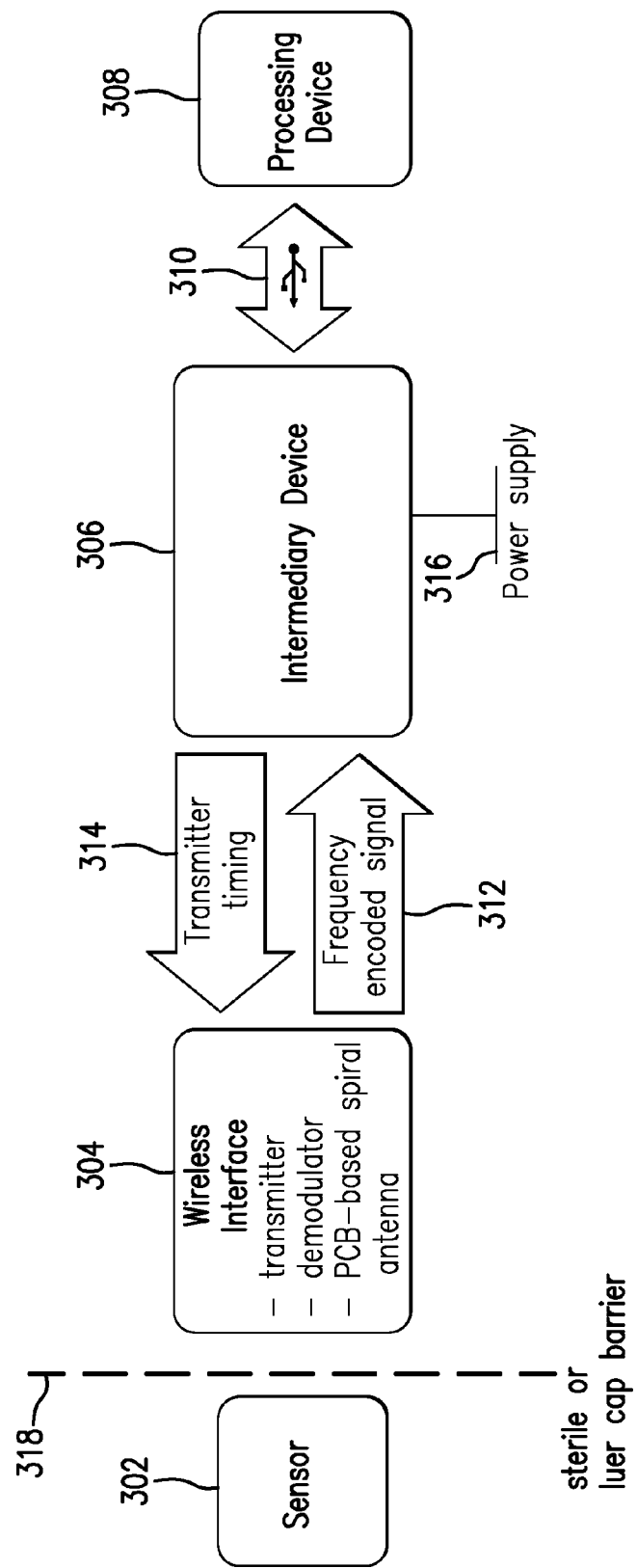
FIG. 3 illustrates a functional representation of a sensor system according to embodiments of the present invention.

In accordance with other aspects, sensors for gaseous applications can also be configured. For example, an oxygen indicator such as ruthenium biphenylphenanthroline or others could be configured into the sensor and the sensor assembly 102 would become an oxygen sensor—either for dissolved oxygen in a fluid line or in a gaseous line. Indeed, according to various embodiments of the present invention, the sensor assembly 102 could be configured to measure any blood or bodily fluid borne biomarker. Additionally, the sensor, according to some embodiments, could be designed to measure the color, refraction index, salinity, pH, affinity regonite elements such as antibodies, ion exchange, or covalent bonding FIG. 3 illustrates a functional representation of a sensor system according to embodiments of the present invention. The mounted sensor 302 can be mounted within a sterile or luer cap barrier 318. A wireless interface 304 (which can include a transmitter, a demodulator, and the primary coil) can be placed within coupling distance of the internal coil 206 of sensor 302 and used to wirelessly excite the sensor 302 and receive sensor data from the sensor 302. In one embodiment of the present invention, the wireless interface 304 can be mounted on the back of sterile or luer cap barrier 318 and provide power to and communication with the sensor through the primary coil. The sensor can be energized by a power amplifier (contained, for example, in drive circuitry) and the primary coil 116. The wireless interface may contain a demodulator (e.g., AM or FM demodulator) that re-encodes the frequencies from the sensor into a digital pulse stream. The wireless interface 304 can then transmit a signal to a processing device 308. According to some embodiments of the present invention, the wireless interface transmits the signal 312 to the processing device 308 though an intermediary device 306 such as, for example, a USB dongle. The USB dongle can be programmed to send signals that drive the power amplifier, perform signal processing on receiving signals, and then interface with the processing device 308 through serial, USB communication, or wireless communication. In some embodiments, the intermediary device 306 communicates information 314 to the wireless interface 304 for the purposes of, e.g., transmitter timing.

In other embodiments, the intermediary device 306 could also be a wireless communications device, network communications device, or any other suitable means for conveying the signal to the processing device. Additionally, according to other embodiments of the invention, the sensor system does not utilize intermediary device 306, but wireless interface 304 transmits the signal directly to the processing device 308 via a direct connection.

Wireless interface 304 may form part of a reading device, according to embodiments of the invention. Each reading device can be associated with a single sensor. However, one advantage of the present application is that many sensors can be installed at multiple points within a processing line such as a soft drink or beverage plant for quality monitoring. According to the present invention, a single reading device can be multiplexed into a host computer in order to read many sensors at preset intervals for master control or monitoring system. Additionally, for applications requiring infrequent sampling intervals, the reading device may be a hand-held device capable of being carried around periodically, according to some embodiments of the present invention.

While FIG. 1 illustrates the drive circuitry 110 and the primary coil 116 housed within the circuit housing 114, in some embodiment, the primary coil and the drive circuitry could be disposed in a separate reading device external to the circuit housing. Such an arrangement is illustrated in FIG. 6.

Figure 6:
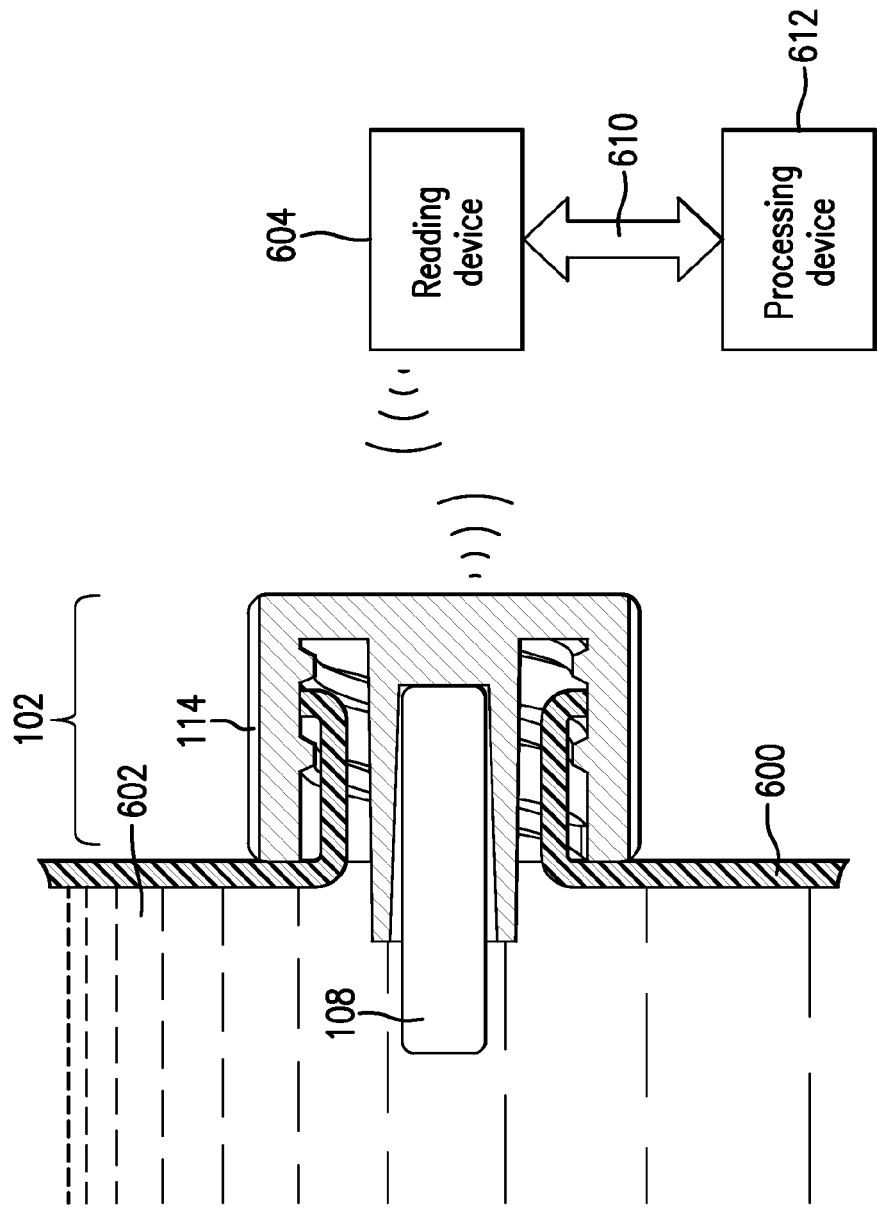
FIG. 6 illustrates a functional representation of a sensor system according to embodiments of the present invention.

FIG. 6 is a functional representation of a sensor system according to embodiments of the present invention. As shown, the sensor assembly 102 is disposed against the side of a medium-containing device 600 such that the optical sensor 108 is in contact with medium 602. Sensor assembly housing 114 abuts the side 600 such that a substantially leak-proof or airtight seal is formed.

In operation, reading device 604 can be placed in close proximity (e.g., within coupling distance) to sensor assembly 102. Reading device 604 is in wireless communication with optical sensor 108 and can be capable of relaying information to processing device 612 via communications channel 610. According to some embodiments of the present invention, communications channel 610 is a wireless communications interface. In other embodiments, communications channel 610 could also be any sort of communications channel such as a coaxial cable, serial connection, USB cable, direct connection, or any other suitable means of transmitting data from one place to another.

Figure 7C:
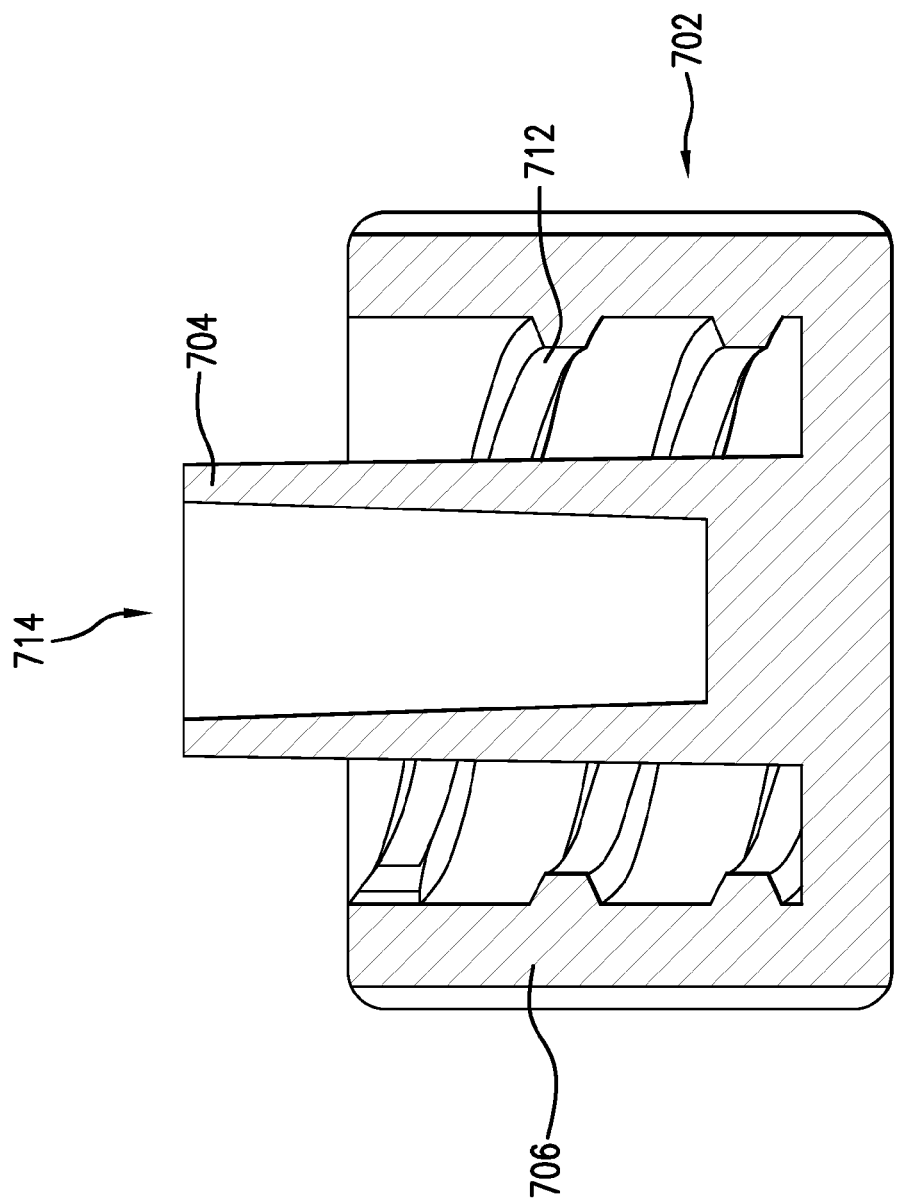

According to some embodiments of the present invention, housing 114 comprises a luer fitting. FIGS. 7(a)-(c) depict a luer fitting according to embodiments of the present invention from different angles. Luer fittings (commonly known as "luer," "luer taper," or "luer lock") are used in a variety of applications. For instance, luer fittings are used in syringes, catheters, blood bags, pumps, fermentation sampling syringes, chromatography fittings, and many other fluid (e.g., liquid or gas) handling circuits and apparatus. Luer fittings of standard dimensioning are used throughout medical, food, and industrial applications as simple and universally compatible means of small line liquid or gas connection. Use of luer fittings as the housing, in certain embodiments of the present invention, allows the sensor assembly to be easily installed to operate within medical and industrial fluid circuits utilizing a universal standard.

According to some embodiments, a luer fitting 702 may comprise an external sleeve 706 and a tapered cone 704. According to some embodiments, the cone can have a standard taper of approximately 6%. In other embodiments, the cone can have a taper of other angles. The luer fitting 702 may also include a luer cap 702b, which can join with the main body of the luer 702a. According to embodiments of the present invention, the luer cap may include a via 710 that allows a hardwired connection between primary coil 716, which has been mounted inside of cap 702b, and the drive circuitry. Alternatively, both the primary coil 716 and the drive circuitry may be located outside of the cap 702b. In other embodiments, there is no via in the luer cap and the system utilizes a wireless connection as disclosed herein.

FIG. 7(c) illustrates one embodiment of the luer fitting 702 in a cut-away perspective. As can be seen, cone 704 and external sleeve 706 form a tapered cavity 708. According to some embodiments of the present invention, the tapered cavity 708 can be smooth. However, as shown in FIG. 7(c), tapered cavity 708 may also include locking threads 712, which can form a more secure fitting in some cases. Sensor 108 can be mounted partially within cavity 714.

Figure 4:
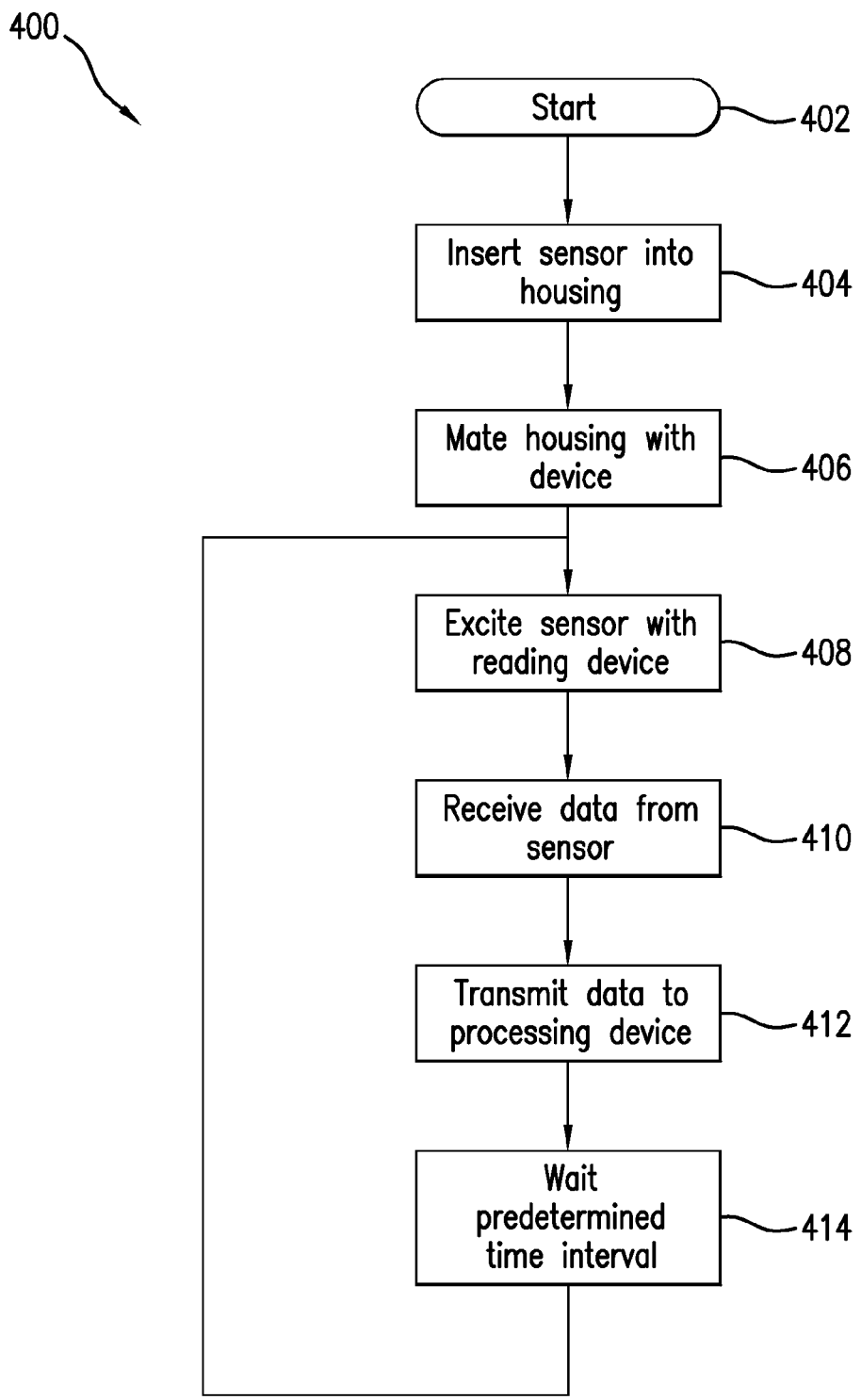
FIG. 4 illustrates a flow chart for measuring the presence of an analyte in a medium according to embodiments of the present invention.

The sensor assembly can be used to take measurements of an analyte in a number of different ways. FIG. 4 illustrates a flow chart representing one such representative method. According to method 400, once the sensor 108 is inserted into its housing 114 at step 404, the housing can be mated with a device at step 406. The device preferably contains or is in communication with an analyte-containing medium and the housing 114 is preferably mated with the device such that the sensor 108 is brought into contact with the analyte containing medium. The sensor can be excited with reading device 604 at step 408. The sensor 108 then takes its measurements of the analyte and sends the information to the reading device, which is received at step 410. The reading device can then transmit the data to the processing device 612 at step 412. According to some embodiments, the process 400 can terminate at step 412. According to other embodiments, however, the reading device 604 is configured to take multiple measurements using the sensor 108 over time at predetermined time intervals. In such an embodiment, the reading device 604 can then wait a predetermined time interval at step 414 before looping back to step 408 to excite the sensor 108 again.

Figure 5:
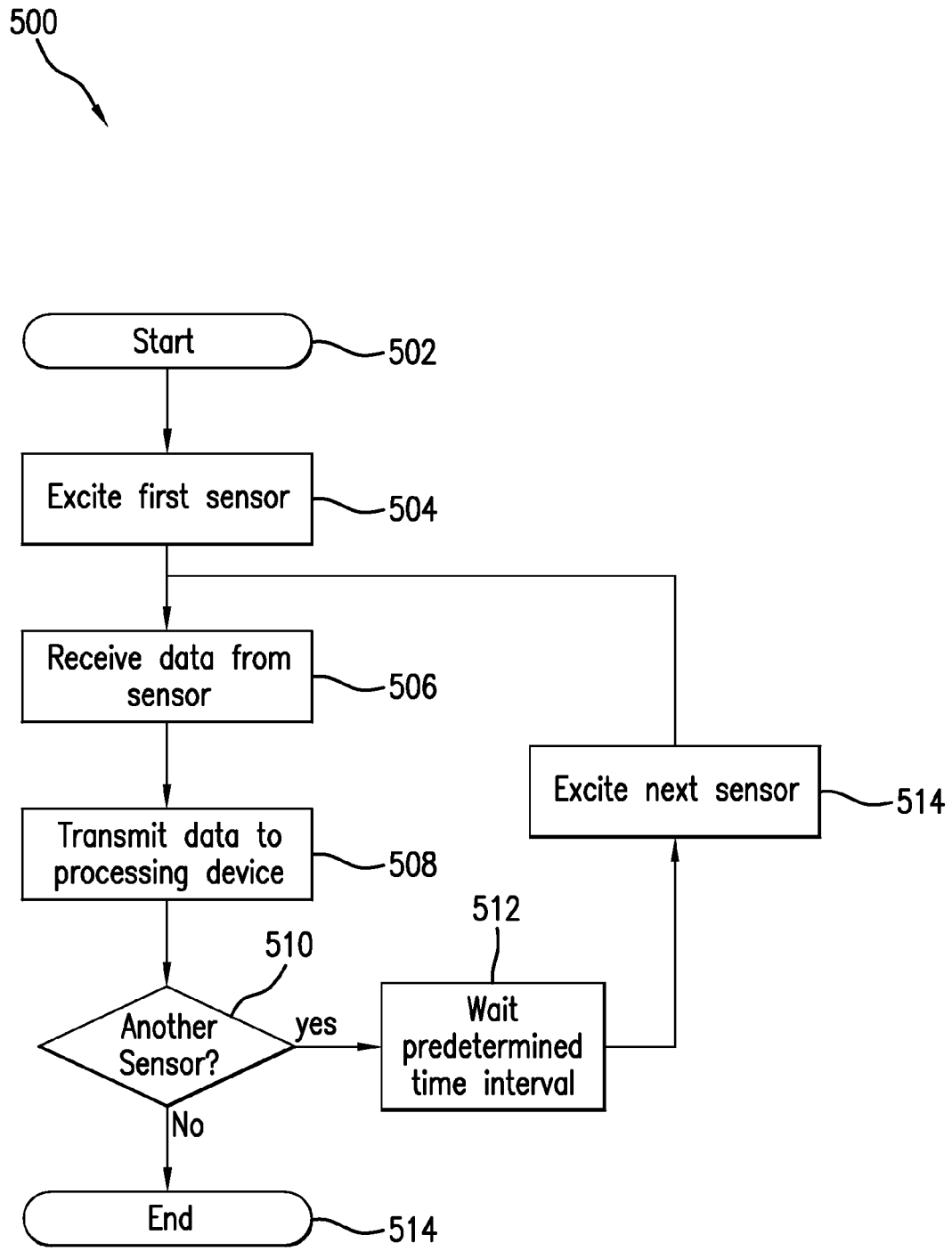
FIG. 5 illustrates a flow chart for measuring the presence of an analyte in a medium according to embodiments of the present invention.

FIG. 5 depicts a method of reading multiple sensors using the same reading device 604 according to an embodiment of the present invention. According to the method 500, a first sensor is excited at step 504. When data is received by the reading device 604 at step 506, it is transmitted to the processing device 612 at step 508. At this point, a determination can be made regarding whether another sensor needs to be read at step 510. If another sensor does not have to be read, then the process ends at step 514. If another sensor does have to be read, then the reading device 604 can wait a predetermined time interval at step 512 prior to exciting the next sensor at step 514. After that, the process is repeated at step 506.

As mentioned previously, there are a number of different applications of the sensor assembly, sensor systems and methods of the present invention. For example, in medicine, syringes, catheters, blood bags, and pumps all contain mediums that need to be monitored for analytes of interest. Additionally, other applications, such as fermentation sampling syringes, chromatography fittings, and many other fluid handling circuits and apparatus all require analyte monitoring. Many of these applications use the standard luer fittings.

For example, a syringe's barrel connects to a needle by means of a luer fitting that is molded into the syringe plunger (frequently male) and into the needle (frequently female). There are commonly available fittings of all kinds made to this luer standard including "Y" and "T" connectors (both male and female), valves, manifolds, columns, reservoirs, etc. Furthermore, luer fittings are used for both fluid and gas circuits. By creating a sensor so tiny as to fit within a luer taper, any medical, laboratory, or industrial application using luer standard fittings can easily install a sensor into their fluid or gas circuit by simply utilizing an inexpensive luer "T" or any luer female fitting interface.

Figure 9:
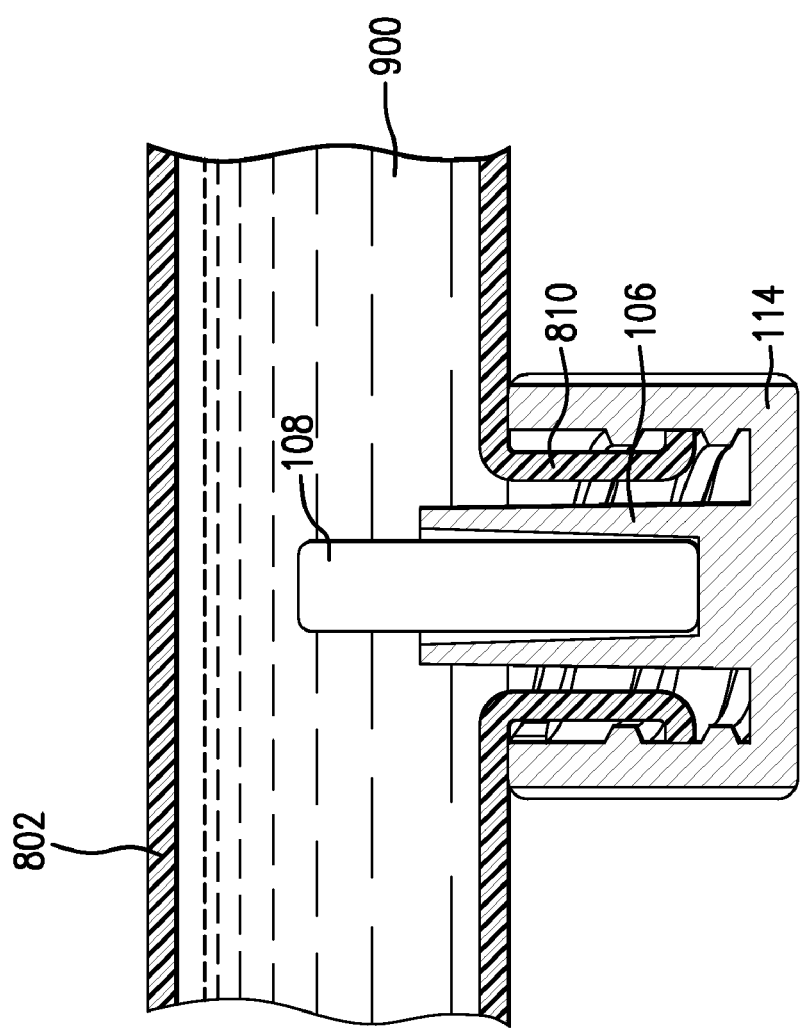
FIG. 9 illustrates a sensor system according to embodiments of the present invention.

FIG. 8 illustrates one use of the sensor assembly 102 according to embodiments of the present invention. In FIG. 8, device 812 is a syringe comprising a barrel 806, an open end 808, a "T" joint 802, and a tip 804 having a needle 814. Open end 808 and tip 804 are designed to join with joint 802. Similarly, the mating portion 106 of the housing 114 is configured to mate with the bottom portion 810 of joint 802. According to embodiments of the present invention, the housing 114 is mated with tube portion 802 such that when a fluid flows from barrel 806 to tip 804, the fluid (or analyte containing medium) comes into contact with sensor 108. According to some embodiments of the present invention, the open end 808 and tip portion 804 are luer fittings FIG. 9 illustrates a partial cut-away of the sensor assembly 102 inserted into the bottom portion 810 of joint 802 according to embodiments of the present invention. As can be seen, the sensor assembly 102 is configured such that sensor 108 is disposed within analyte-containing medium 902.

While FIGS. 8 and 9 depict device 812 as a syringe, this is meant to be a non-limiting example merely to illustrate the principles behind the functioning of the present invention. Indeed, a person of ordinary skill in the art would understand that the device that mates with sensor apparatus 102 could be anything capable of holding an analyte-containing medium. For instance, according to some embodiments of the present invention, the device is a fluid line, conduit, tube, or catheter. According to other embodiments, the device could be a vessel or container.

Beyond the ability to monitor analytes (e.g., glucose) from in-stream and in real time, there are a host of practical advantages in a sensor configuration using a luer connection. Although the sensor assembly with the luer cap can be configured to operate wired or wirelessly, the wireless embodiment has the great advantage of maintaining a monolithic barrier within a sterile fluid (or gas) line. Via the same passive telemetry and remote power system developed for the implantable system, the sensor embedded in the luer cap requires no penetrations across the barrier for power or signal to pass. See, for example, U.S. Pat. No. 6,400,974, which is incorporated herein by reference in its entirety.

In an application requiring continuous monitoring (such as in an intensive care unit), the sensor assembly 102 can always remain in communication with a reading device via an external antenna. This antenna can be dedicated to one sensor according to embodiments of the present invention.

Depending on the application, the sensor of the present invention may or may not be disposable after use. For example, in an ICU environment for a patient over days or weeks, the sensor (but not the reader, according to some embodiments) could be disposed to prevent any possible cross contamination. However, for many non-medical applications (e.g., food or beverage manufacturing), it may be appropriate to clean and reuse the sensors 108 many times.

One of ordinary skill in the art would understand that sensors that use transduction mechanisms other than fluorescence are possible. For instance, according to some embodiments of the present invention, sensors detect the presence of an analyte by using an appropriate sensor to detect colorimetric, refractive index, turbidity, backscatter, or absorbance.

According to other aspects of the present invention, the sensing apparatus can be configured as a stand-alone sensor platform. In this embodiment, the apparatus could be configured to stand alone and have remote, radio frequency, or uplinking telemetry capability to allow distance monitoring. This embodiment is useful for applications such as pipeline, hydroponics, water purification, and pollution monitoring (amongst others). By use of the sensor assembly of the present invention, which uses a standard luer in certain embodiments, the sensor cap can easily be removed and replaced or changed within a line without disrupting fluid flow or system pressure for industrial applications.

Thus, a number of preferred embodiments have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:

1. A sensing apparatus comprising:
a housing having an external sleeve and a mating member housed within said external sleeve;
an optical-based sensor capable of measuring the presence of an analyte in an analyte containing medium, said sensor disposed within said mating member, wherein said sensor includes a body, internal circuitry, and an internal coil housed within its body, said internal coil being configured to wirelessly receive electrical power from an external power supply; and
drive circuitry configured to communicate power to and receive data from said sensor,
wherein said mating member is configured to mate with a device in contact with said medium containing said analyte to be measured such that said optical-based sensor is capable of contacting said analyte containing medium.

2. The sensing apparatus according to claim 1, wherein said sensor further comprises:
a light source for introducing light into a fluorescent indicator that interacts with said medium; and
a photodetector for detecting light emitted by said fluorescent indicator in response to the introduced light, and for outputting a signal proportional to the detected light, the response of the fluorescent indicator varying in accordance with the presence and concentration of an analyte in the medium.

3. The sensing apparatus according to claim 2, wherein said data comprises said signal output from said photodetector.

4. The sensing apparatus according to claim 1, wherein said drive circuitry is further configured to communicate data from said sensor to an external processing device.

5. The sensing apparatus according to claim 4, wherein said drive circuitry communicates said data from said sensor to said external processing device via a wireless communications interface.

6. The sensing apparatus according to claim 1, wherein said primary coil is disposed within said housing.

7. The sensing apparatus according to claim 1, wherein said primary coil is printed on a PCB substrate and mounted within coupling distance of said internal coil.

8. The sensing apparatus according to claim 1, wherein the housing is a Luer fitting.

9. The sensing apparatus according to claim 8, wherein the Luer fitting has an approximately six percent taper.

10. The sensing apparatus according to claim 1, wherein said analyte is glucose.

11. The sensing apparatus according to claim 1, wherein said sensor is configured to measure a more than one analyte.

12. The sensing apparatus according to claim 1, wherein said drive circuitry is configured to communicate power to and data from said sensor by electromagnetic induction.

13. The sensing apparatus according to claim 1, wherein said device is a syringe.

14. The sensing apparatus according to claim 1, wherein said device is a fluid line.

15. The sensing apparatus according to claim 1, wherein said drive circuitry is further configured to communicate data to said sensor.

16. A sensor system comprising:
a plurality of optical-based sensors for measuring the presence of an analyte in an analyte containing medium, each of said sensors being disposed a housing having an external sleeve and a mating member housed within said external sleeve, wherein each of said sensors includes a body, internal circuitry, and an internal coil housed within its body, said internal coil being configured to receive electrical power from an external power supply and to transmit data;
at least one reading device comprising drive circuitry coupled to a primary coil, said primary coil configured to transmit power to and receive data from said internal coil of said plurality of optical-based sensors; and
a processing device configured to interface with said reading device in order to receive said data from at least one of said plurality of optical-based sensors;
wherein said mating member of said housing is configured to mate with a device in contact with said medium containing said analyte to be measured such that said optical-based sensors are brought into contact with said analyte containing medium.

17. The sensor system according to claim 16, wherein said sensors further comprise:
a light source for introducing light into a fluorescent indicator that interacts with a medium; and
a photodetector for detecting light emitted by said fluorescent indicator in response to the introduced light, and for outputting a signal proportional to the detected light, the response of the fluorescent indicator varying in accordance with the presence and concentration of an analyte in the medium.

18. The sensor system according to claim 17, wherein said data comprises said signal output from said photodetector.

19. The sensor system according to claim 16, wherein said primary coil is printed on a PCB substrate and mounted within coupling distance of said internal coil of one of said plurality of optical-based sensors.

20. The sensor system according to claim 16, wherein said reading device communicates said data from said sensor to said processing device via a wireless communications interface.

21. The sensor system according to claim 16, wherein at least one of said housings is a Luer fitting.

22. The sensor system according to claim 16, wherein said analyte is glucose, O2 or CO2.

23. The sensor system according to claim 16, wherein the optical-based sensor of said at least one sensor apparatus is configured to measure more than one analyte.

24. The sensor system according to claim 16, wherein each sensor has a separate reading device associated with it.

25. The sensor system according to claim 16, wherein said reading device comprises a portable device capable of reading more than one of said plurality of sensors.

26. The sensor system according to claim 16, wherein said reading device is configured to read more than one of said plurality of sensors at a different preset interval.

27. The sensor system according to claim 16, wherein the reading device is configured to send data to said plurality of optical-based sensors.

28. A method of measuring the presence and concentration of an analyte in a medium comprising:
providing a sensing apparatus comprising a housing having an external sleeve and a mating member disposed within said external sleeve, said sensing apparatus further comprising an optical-based sensor disposed within the mating member of said housing, said optical-based sensor including a body, internal circuitry, and an internal coil housed within its body, wherein said internal coil is configured to receive electrical power from an external power supply;
mating said sensing apparatus with a device that configured to be in fluid communication with said medium containing said analyte to be measured,
exciting said internal coil by electromagnetic induction using a reading device;
receiving at the reading device data from the optical-based sensor relating to the presence of an analyte in a medium; and
transmitting said data to a processing device.

29. The method of measuring the presence and concentration of an analyte according to claim 28, wherein the internal coil is excited at predetermined intervals.

30. The method of measuring the presence and concentration of an analyte according to claim 29, wherein said data is transmitted to said processing device wirelessly.

31. The method of measuring the presence and concentration of an analyte according to claim 30, wherein said optical-based sensor comprises:

a light source for introducing light into a fluorescent indicator that interacts with a medium; and
a photodetector for detecting light emitted by said fluorescent indicator in response to the introduced light, and for outputting a signal proportional to the detected light, the response of the fluorescent indicator varying in accordance with the presence and quantity of an analyte in the medium.

32. The method of measuring the presence and concentration of an analyte according to claim 31, wherein said data comprises said signal output from said photodetector.

33. The method of measuring the presence and concentration of an analyte according to claim 29, wherein said housing is a Luer fitting.

34. The method of measuring the presence and concentration of an analyte according to claim 29, wherein the device is a fluid line.

35. The method of measuring the presence and concentration of an analyte according to claim 28, further comprising the step of sending data to said sensor.

36. A sensing apparatus comprising:
a housing having an cavity disposed in an outside surface of the housing;
an optical-based sensor capable of measuring the presence of an analyte in an analyte containing medium, said sensor disposed within said cavity in said housing, wherein said sensor includes a body, internal circuitry, and an internal coil housed within its body, said internal coil being configured to receive electrical power from an external power supply; and
drive circuitry configured to communicate power to and receive data from said sensor,
wherein said housing is configured to connect with a device in contact with said medium containing said analyte to be measured such that said optical-based sensor is capable of contacting said analyte containing medium.

37. The sensing apparatus of claim 36, wherein the internal coil is configured to wirelessly receive electrical power from the external power supply, and the drive circuitry configured to wirelessly communicate power to and data from said sensor.

38. The sensing apparatus of claim 36, wherein the internal coil is configured to receive electrical power from the external power supply, and the drive circuitry configured to communicate power to and data from said sensor, through a communication wire.

39. The sensing apparatus of claim 36, wherein said drive circuitry is further configured to send data to said sensor.

* * * * *